United States Patent [19]  [11] Patent Number: 4,854,319
Tobin  [45] Date of Patent: Aug. 8, 1989

[54] COOLING APPAREL

[75] Inventor: Cullin S. Tobin, Phoenix, Ariz.

[73] Assignee: Chilly Bones, Inc., Scottsdale, Ariz.

[21] Appl. No.: 123,306

[22] Filed: Nov. 20, 1987

[51] Int. Cl.$^4$ ............................................. A61N 3/00
[52] U.S. Cl. .................................... 128/380; 128/402
[58] Field of Search ............................. 128/399–403, 128/379, 380, 384; 383/901; 62/530

[56] References Cited

U.S. PATENT DOCUMENTS

| | | | |
|---|---|---|---|
| 2,043,327 | 6/1936 | Miller | 128/403 |
| 3,545,230 | 12/1970 | Morse | 62/530 |
| 3,885,403 | 5/1975 | Spencer | 128/403 |
| 3,889,684 | 6/1975 | Lebold | 128/402 |
| 4,055,188 | 10/1977 | Felton | 128/402 |
| 4,204,543 | 5/1980 | Henderson | 128/402 |
| 4,326,533 | 4/1982 | Henderson | 128/402 |
| 4,381,025 | 4/1983 | Schooley | 128/402 |
| 4,404,820 | 9/1983 | Romaine | 62/530 |
| 4,527,566 | 7/1985 | Abare | 128/402 |
| 4,556,055 | 12/1985 | Bonner | 128/402 |
| 4,592,358 | 6/1986 | Westplate | 128/402 |
| 4,625,729 | 12/1986 | Roney | 128/402 |
| 4,676,247 | 6/1987 | Van Cleve | 128/402 |

FOREIGN PATENT DOCUMENTS

| | | | |
|---|---|---|---|
| 1185811 | 3/1970 | United Kingdom | 128/402 |
| 2158936 | 11/1985 | United Kingdom | 128/402 |

Primary Examiner—Edward M. Coven
Assistant Examiner—Mark S. Graham

[57] ABSTRACT

Sports wear apparel in the form of wrap around headbands or the like is provided with a tube of plastics sheet material defining pockets filled with refrigerant gel. The tube is composed of a thin plastics material film coated and covered on the outside with a nonabsorbent and nonporous foam integrally bonded on the film. This foam meters heat transfer from the refrigerant gel to the skin of the wearer and provides pockets which trap moisture from the skin and then permit the moisture to evaporate as the cooling capacity of the gel diminishes. This evaporation extends the cooling capacity of the apparel. The ends of the tube are adapted to overlap and are equipped with fasteners such as hook and loop tapes to secure the tube in wrapped around condition on the wearer.

8 Claims, 1 Drawing Sheet

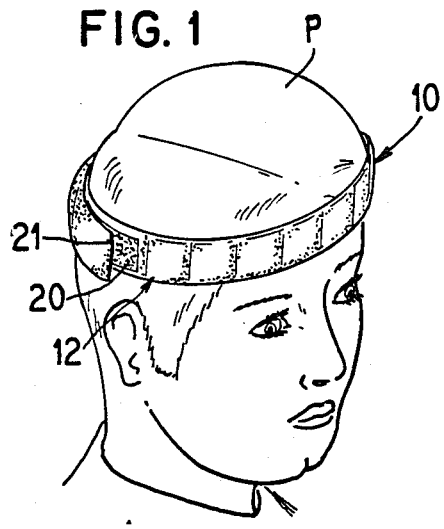
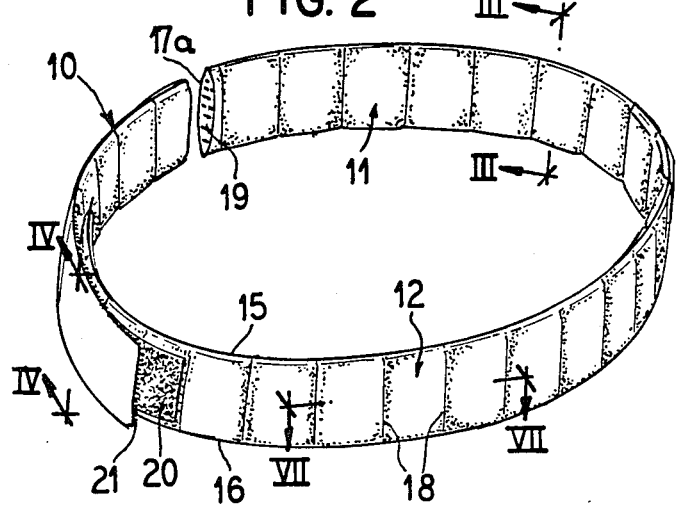
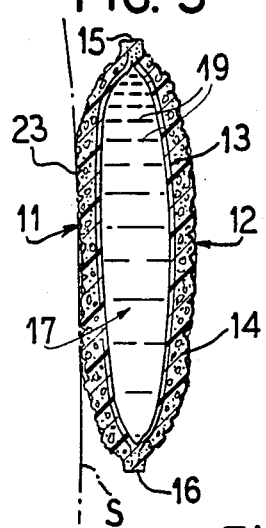
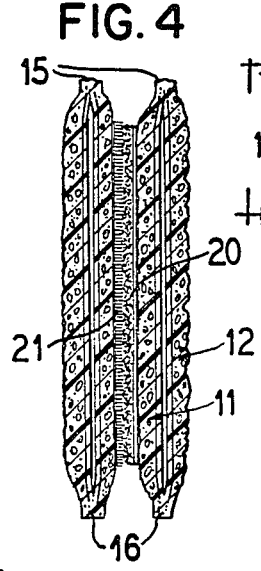
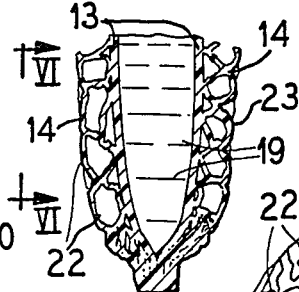
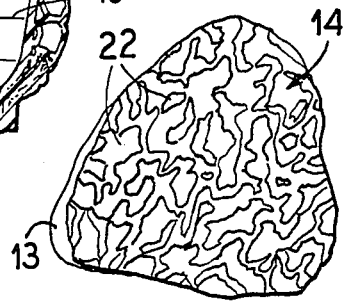
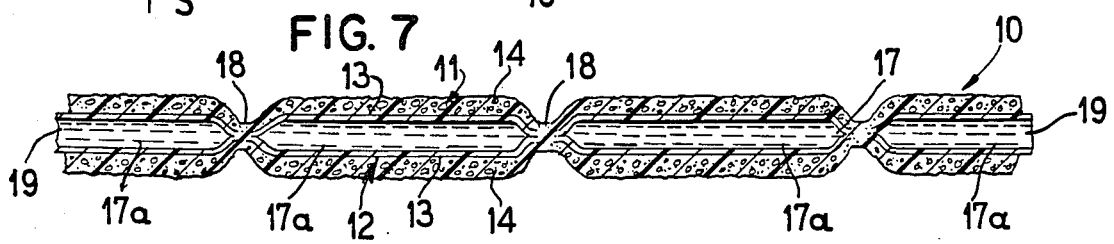
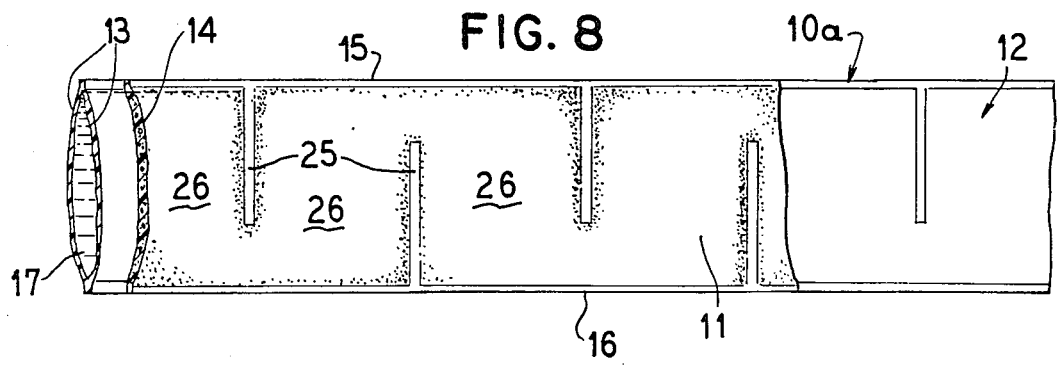

COOLING APPAREL

RELATED APPLICATION

This application is related to the Cullin Sean Tobin prior U.S. patent application entitled "Cooling Apparel", Ser. No. 76,912, filed July 23, 1987, abandoned.

FIELD OF THE INVENTION

This invention relates to coolant or refrigerant equipped therapeutic wearing apparel adapted to be wrapped around and cool underlying adjacent parts of the body while monitoring heat transfer to insulate the body against initial cold shock and then condensing and trapping moisture for subsequent evaporation to prolong and enhance the cooling effect on the body. Specifically this invention deals with sports wear in the form of tubular headbands, wristbands, anklebands and the like, containing pockets of refrigerant gel and formed from a laminated plastics material having a blister-like lattice textured nonabsorbing foam outer face backed by an impervious film sealing the refrigerant gel while the foam surface engages the skin of the wearer, slows down heat transfer to protect the skin from initial cold shock from the frozen or very cold refrigerant gel and then condenses and traps moisture from the skin for subsequent evaporation to prolong the cooling effect of the gel.

BACKGROUND OF THE INVENTION

Coolant or refrigerant equipped therapeutic devices are known in the art, for example, in the U.S. Pat. Nos. 4,204,543, to Henderson, 4,381,025 to Schooley, and 4,592,358 to Westplate. The prior known coolant equipped therapeutic devices, however, either provide absorbent material between the coolant and the skin of the wearer or expose the skin of the wearer directly to the planar surfaces of the coolant containing pockets. The absorbent material soaks up and quickly dissipates moisture from the skin of the wearer. It acts as a heat transfer barrier that will also dissipate the cooling capacity of the coolant or refrigerant material. On the other hand, the direct contacting of the smooth planar impervious plastics or the like packaging material for the refrigerant gel against the skin of the wearer causes an acute thermo shock which could freeze the material to the skin creating not only discomfort but also skin damage.

It will therefore be an improvement in this art to provide therapeutic cooling apparel containing refrigerant material in a flexible impervious tube adapted to be wrapped around the part of the body to be cooled and having a foam surface directly engaging the skin of the wearer and providing a blister-like lattice texture condensing and trapping moisture for subsequent evaporation to prolong the cooling effect of the refrigerant material.

It would be a specific improvement in this art to provide tubular headbands, wristbands, and anklebands composed of flexible polyolefin film housing pockets of refrigerant gel and having an outer surface composed of polyolefin foam spot welded on the film and providing a lattice texture face for directly engaging the skin of the wearer to prevent initial thermo shock and to condense and trap moisture.

SUMMARY OF THE INVENTION

This invention now provides improved therapeutic wearing apparel containing a coolant material such as refrigerant gel, preferably in the form of wraparound, head, wrist, ankle and the like bands having lattice texture nonabsorbent skin engaging surfaces to directly engage the skin of the wearer to monitor heat transfer, condense and trap moisture and permit evaporation of the condensation to prolong the cooling effect of the refrigerant gel. The textured skin engaging surface accommodates breathing of the skin covered by the band. The preferred band material is a synthetic polymer film or sheet, the outer face of which has the same or a different synthetic polymer foam spot welded thereon to form a lattice texture lamination on the base sheet or film. A specifically preferred material is a polyethylene film about 1½ to 4 mm. thick having a polyethylene foam spot welded on one face thereof forming a lattice textured laminate about 1/16 to ⅛ inch thick. The foam material, like the base film material, is nonabsorbent and nonporous. The base film is on the inside of the tubular band so that the lattice textured foam directly contacts the skin of the wearer.

A suitable plastics band material is supplied by Sentinel Foam Company of Dallas, Tex.

The tubular band is conveniently formed from a pair of superimposed strips of the plastics material, heat sealed along their edges to provide an open ended tube and transversely heat sealed at spaced intervals along its length to form refrigerant receiving pockets. The transverse heat seals can extend completely across the strips to isolate the pockets and provide bending zones between the pockets so that the band will conform to the body part around which it is wrapped even when the refrigerant gel in the pockets is frozen to a hard stiff state.

In another embodiment of the invention the spaced transverse heat seals extend alternately from each longitudinal side edge of the tube to provide a serpentine continuous pocket along the length of the tube.

The ends of the tube are heat sealed and hook and loop ("VELCRO") fastener tapes are secured along each end margin of the tube. The fastener tapes are preferably secured to opposite faces of the end portions of the tube so that when the bands are wrapped around the wearer, the mating fastener strips will be overlapped for engagement.

Alternatively the fastener tapes can be secured to the same side or face of the tube so that when the tube end portions are secured together they will project as a tail from the body encircled portion of the band.

The end portions of the band carrying the fastener tapes are preferably not filled with the refrigerant gel. The tubular band can be provided in assorted lengths and widths. Band heights of 2 to 3 inches are ample for headbands. Wristbands and anklebands can be wider and, of course, the widths can be extended to cover major lengths of the arms and legs. Headband lengths of 22 to 30 inches are sufficient to accommodate a wide variety of head sizes. The lengths of the "VELCRO" tape, of course, accommodate a wide range of sizes for the wraparound portions of the band.

The foamed plastics film material is tough, has high tensile and bursting strength under a wide range of temperature conditions, retaining its flexibility even when the refrigerant gel contents are hard frozen.

The bands of this invention are made available for use by storage in the freezing compartment of a conventional refrigerator and the foam plastics material provides a prolonged use for the cold or frozen refrigerant gel.

The invention will be further understood from the attached drawings showing several preferred embodiments of the invention.

ON THE DRAWINGS

FIG. 1 is a perspective view of a coolant band of this invention in operative position around the head of a user.

FIG. 2 is a perspective view of the band with a portion cut away to show the interior of a pocket and illustrating the manner in which the "VELCRO" tapes are adjustably overlapped and releasably attached together.

FIG. 3 is a transverse sectional view along the line III—III of FIG. 2 and illustrating the manner in which the foam on the interior face of the band confronts the skin of the wearer.

FIG. 4 is a transverse sectional view along the line IV—IV of FIG. 2.

FIG. 5 is a view similar to FIG. 3 but greatly magnified to emphasize the latticed network of the exterior foam on the base film.

FIG. 6 is a view of the surface of the band along the line VI—VI of FIG. 5.

FIG. 7 is a longitudinal sectional view along the line VII—VII of FIG. 6.

FIG. 8 is a fragmentary side elevational view of a portion of a modified band construction with parts broken away to show underlying details.

AS SHOWN IN THE DRAWINGS

The headband 10 of FIGS. 1 and 2 is illustrated in a wraparound use position to surround the head of a person P during exercise such as jogging. It will, of course, be understood that the band 10 is a therapeutic device serving to cool all parts of the body around which it is wrapped and useful for reducing of swelling, pain, fever and the like.

The band 10 is formed from a pair of overlying strips 11 and 12 of plastics material composed of an inner smooth planar faced film 13 and a thicker outer foam layer 14 spot welded on the outer face of the film. The two strips are sealed together along their longitudinal edges as illustrated in 15 and 16 forming a tubular chamber 17 between the strips. Alternately the band 10 can be formed from a single wide strip folded over along its length and then having its overlapped free edges heat sealed together.

Transverse heat seals or welds 18 in spaced parallel relation along the length of the band divide the tubular chamber 17 into a plurality of individual pockets 17a with the seals providing transverse bending zones or hinges between the pockets.

The pockets are filled with a coolant material such as a refrigerant gel 19 of high endothermic capacity. Such materials frequently include carboxymethyl cellulose. Commercially available refrigerant gels are now on the market under the tradename "Blue Ice" by Gott Corporation of Winfield, Kan.; "Lifoam" by Lifoam Corporation of Baltimore, Md., and "Ice-Pack-Gel" by Stanbel Inc. of Springfield, Mass. Some of these gels hold their shape even when fully thawed while others thaw into a flowable slush.

As illustrated in FIGS. 1 and 2, the ends of the band 10 are overlapped in their use position. The outer face of the underlapped portion and the inner face of the overlapped portion have confronting mating tapes 20 and 21 of hook and looped fastener material such as "VELCRO" secured thereon as by adhesive or the like so that the hooks of one strip will mate with the loops of the other strip to releasably secure the overlapped portions together. The strips 20 and 21 preferably have a substantial length of several inches to accommodate a variation of the lengths of the overlaps thereby expanding or contracting the loop or ring of the headband to snugly wraparound different sized heads.

As better shown in the magnified views of FIGS. 5 and 6, the inner film 13 is smooth and planar while the outer foam layer 14 is an open lattice of foam particles 22 presenting an irregular blister-like surface 23. This irregular surface 23 directly confronts the skin S of the forehead of the person P wearing the band and it will be especially noted that a myriad of pockets are provided between the skin and foam. These pockets will trap moisture from the skin but since the foam is not absorbent the trapped moisture will accumulate until it is sufficiently warm to evaporate. The evaporation brings about an additional cooling effect. The skin covered by the blister-like surface of the band can "breathe" and heat from the body causes moisture to condense on the foam surface to provide a comforting cool moist zone on the skin. Then as the refrigerated gel warms up, this moisture can evaporate to prolong the cooling effect.

It will also be noted that the relatively thick foam layer 14 interposed between the refrigerant gel 19 and the skin S coupled with the interstices of the lattice-like network of the foam provides somewhat of an insulation preventing cold thermo shock to the skin S. The foam, however, does provide a good heat transfer between the gel and the skin, but provides for breathing of the skin which will not cause pain or shock or even damage to the skin, such as might occur by pressing a smooth planar cold surface directly on the skin.

Since both faces of the band are alike, either of them can be pressed against the skin and in the event the trapped moisture becomes excessive the band can be reversed to present the outer face to the skin.

The end portions of the band receiving the tapes 20 and 21 are preferably not filled with refrigerant gel so as to reduce the thickness of the overlapped portions.

As shown in FIG. 8, a modified band 10a constructed of the same material as the band 10 and bearing the same reference numerals as the like components of the band 10, has spaced transverse heat seals 25 which only extend partially across the width or height of the band. These seals alternate from the opposite edges 15 and 16 of the band 10a and divide the tubular chamber 17 into interconnected compartments 26 so that fluid refrigerant gel can flow in a serpentine path in the tubular channel. This arrangement facilitates filling of the tubular chamber 17 with the gel material. Since the adjacent heat seals overlap, the bending zones or hinges provided by the seals will accommodate flexing of the band into a body encircling position even when the refrigerant is frozen solid.

The ends of the band 10a may be equipped with the same fastener devices 20 and 21 provided on the band 10.

From the above description it should be understood that this invention provides a very lightweight inexpensive therapeutic cooling band which monitors heat transfer, traps and condenses moisture from the skin and then evaporates the moisture to prolong the cooling effect.

I claim as my invention:

1. Therapeutic sports wearing apparel which comprises a tube of plastics sheet material having an inner nonabsorbent, nonporous smooth faced flexible film layer and an integral outer moisture impervious foam layer composed of particles covering and bonded to said film layer forming a blister-like lattice surface on the film, a refrigerant gel material encased in said tube, and means on the ends of the tube for wrapping the tube directly around the skin of a user to engage the lattice surface with the skin to form therewith pockets trapping moisture from the skin to provide a cool moist zone on the skin, said outer foam layer being effective to meter heat transfer from the gel to the skin preventing cold shock and said lattice surface accommodating evaporation of moisture trapped in the pockets as the cooling capacity of the refrigerant gel diminishes thereby prolonging the cooling capacity of the apparel.

2. A therapeutic band for wrapping around a portion of the skin of a user which comprises an elongated flexible tube of smooth faced moisture impervious plastics sheet material having an integral outer surface composed of moisture and air impervious nonabsorbent foam with a blister-like lattice of foam particles and pockets between the particles, longitudinally spaced transverse seals along the length of the tube dividing the interior of the tube into a plurality of longitudinally spaced pockets along the length of the tube, refrigerant material in said longitudinally spaced pockets, said transverse seals defining flexible hinges between said longitudinally spaced pockets, tapes of hook and loop fastener material secured to the end margins of the tube cooperating to wrap the tube around the user and compress the outer surface against the skin of the user, said outer surface being effective to prevent cold shock on the skin from the refrigerant material, condense and trap moisture from said skin in said pockets between said foam particles and said pockets between said foam particles being effective to accommodate evaporation of the condensed moisture when the cooling capacity of the refrigerant is dissipated.

3. The wearing apparel of claim 1 wherein the means for wrapping the tube directly around the skin of a user are mating hook and loop fastener tapes secured to the margins of the ends of the tube.

4. The wearing apparel of claim 1 wherein the inner film is a polyolefin plastics material and the outer surface layer is substantially thicker than the film and composed of the same or a different polyolefin material.

5. The therapeutic wearing apparel of claim 2 wherein the spaced transverse seals extend completely across the width of the tube to isolate the pockets.

6. The therapeutic band of claim 2 wherein the transverse seals extend alternately partially inwardly from the opposite longitudinal edges of the tube to provide a serpentine path connecting the pockets.

7. The therapeutic band of claim 2 wherein the plastics material is a laminate composed of a smooth planar thin film defining the interior of the tube and the outer foam surface is integrally coated on to the film.

8. The band of claim 2 wherein the foam is an insulator metering cold transfer between the refrigerant material and skin of the user.

* * * * *